United States Patent
Peng et al.

(10) Patent No.: US 11,181,597 B1
(45) Date of Patent: Nov. 23, 2021

(54) AUTOMATIC ANALYSIS SYSTEM ON MAGNETIC RESONANCE IMAGING AND OPERATION METHOD THEREOF

(71) Applicants: Taipei Medical University (TMU), Taipei (TW); TAIPEI VETERANS GENERAL HOSPITAL, Taipei (TW)

(72) Inventors: Syu-Jyun Peng, Hsinchu County (TW); Chih-Ying Huang, Kaohsiung (TW); Cheng-Chia Lee, Taipei (TW); Huai-Che Yang, Taipei (TW); Hsiu-Mei Wu, Taipei (TW)

(73) Assignees: Taipei Medical University (TMU), Taipei (TW); TAIPEI VETERANS GENERAL HOSPITAL, Taipei (TW)

( * ) Notice: Subject to any disclaimer, the term of this patent is extended or adjusted under 35 U.S.C. 154(b) by 0 days.

(21) Appl. No.: 17/092,348

(22) Filed: Nov. 9, 2020

(30) Foreign Application Priority Data

Sep. 30, 2020 (TW) .................................. 109134258

(51) Int. Cl.
*G06K 9/00* (2006.01)
*G01R 33/56* (2006.01)
(Continued)

(52) U.S. Cl.
CPC ..... *G01R 33/5602* (2013.01); *G01R 33/5608* (2013.01); *G06N 7/005* (2013.01);
(Continued)

(58) Field of Classification Search
CPC .. G01R 33/5602; G01R 33/5608; G06T 7/62; G06T 7/0014; G06T 2207/10088;
(Continued)

(56) References Cited

U.S. PATENT DOCUMENTS

| 2014/0156573 A1* | 6/2014 | Szyperski | .............. G16H 50/20 706/12 |
| 2015/0202330 A1* | 7/2015 | Yang | ..................... A61K 49/14 424/9.34 |

(Continued)

FOREIGN PATENT DOCUMENTS

| CN | 1977049 A | 6/2007 |
| CN | 111526788 A | 8/2020 |

(Continued)

*Primary Examiner* — Atiba O Fitzpatrick
(74) *Attorney, Agent, or Firm* — CKC & Partners Co., LLC

(57) ABSTRACT

The present disclosure provides an operating method of an automatic analysis system on magnetic resonance imaging (MRI), which includes steps as follows. Images are received from of the subject's brain from the MRI machine. Contrast-enhanced T1-weighted images and T2-weighted images are obtained from the images, and the pre-processing is performed on the images. The ratio of T2-weighted images to contrast-enhanced T1-weighted images is calculated to generate contrast-enhanced images. The unsupervised clustering is performed on the region of interest in the contrast-enhanced image to separate a cystic part and a non-cystic part so as to calculate the feature parameters. After radio-surgery is performed on the brain tumor corresponding to the region of interest, the volume change of the tumor is analyzed. The linear regression analysis of the feature parameters and the volume change of the tumor is performed for prognostic evaluation.

10 Claims, 2 Drawing Sheets

(51) Int. Cl.
  *G16H 30/40*    (2018.01)
  *G06T 7/00*     (2017.01)
  *G06N 7/00*     (2006.01)
  *G06T 7/62*     (2017.01)

(52) U.S. Cl.
  CPC .............. *G06T 7/0014* (2013.01); *G06T 7/62* (2017.01); *G16H 30/40* (2018.01); *G06T 2207/10088* (2013.01); *G06T 2207/20076* (2013.01); *G06T 2207/30016* (2013.01); *G06T 2207/30096* (2013.01)

(58) Field of Classification Search
  CPC . G06T 2207/20076; G06T 2207/30016; G06T 2207/30096; G16H 30/40; G06N 7/005
  See application file for complete search history.

(56) References Cited

U.S. PATENT DOCUMENTS

| | | | | |
|---|---|---|---|---|
| 2020/0142017 | A1* | 5/2020 | Taniguchi | G01R 33/5602 |
| 2020/0311926 | A1* | 10/2020 | Tian | G06T 7/0012 |
| 2021/0106250 | A1* | 4/2021 | Du | A61B 5/4082 |

FOREIGN PATENT DOCUMENTS

| | | |
|---|---|---|
| TW | I637187 B | 10/2018 |
| WO | 2020/075991 A1 | 4/2020 |
| WO | 2020/081609 A1 | 4/2020 |

* cited by examiner

AUTOMATIC ANALYSIS SYSTEM ON MAGNETIC RESONANCE IMAGING AND OPERATION METHOD THEREOF

RELATED APPLICATIONS

This application claims priority to Taiwan Patent Application No. 109134258, filed Sep. 30, 2020, the entirety of which is herein incorporated by reference.

BACKGROUND

Field of Invention

The present invention relates to systems and methods, and more particularly, automatic analysis systems on magnetic resonance imaging (MRI) and operating methods thereof.

Description of Related Art

Abnormal proliferation of body cells and tissues may become tumors when they grow in large numbers. The tumor can be benign or malignant. For example, vestibular schwannoma is generally a benign and slow-growing tumor, and its treatment includes radiosurgery, such as Gamma Knife radiosurgery. However, after some patients received radiosurgery, the tumors increased, which caused problems in prognostic evaluation.

In view of above, there is an urgent need in the related field to provide an automatic analysis system and an operating method thereof.

SUMMARY

In one or more various aspects, the present disclosure is directed to automatic analysis systems on magnetic resonance imaging (MRI) and operating methods thereof.

An embodiment of the present disclosure is related to an automatic analysis system on magnetic resonance imaging (MRI). The automatic analysis system includes a memory circuit and a processor. The memory circuit is configured to store at least one instruction. The processor is coupled to the memory circuit, and the processor configured to access and execute the at least one instruction for: receiving a plurality of images of a brain of a subject's brain from a MRI machine; obtaining contrast-enhanced T1-weighted images and T2-weighted images from the images, and performing a pre-processing on the images; calculating a ratio of the T2-weighted images to the contrast-enhanced T1-weighted images to generate contrast-enhanced images; performing an unsupervised clustering on a region of interest in the contrast-enhanced images to separate a cystic part and a non-cystic part so as to calculate feature parameters; analyzing a volume change of a tumor of the brain after radiosurgery is performed on the tumor corresponding to the region of interest; and performing a linear regression analysis of the feature parameters and the volume change of the tumor for prognostic evaluation.

In one embodiment of the present disclosure, the pre-processing performs a bias correction on the images, and then co-registers the T2-weighted images to the contrast-enhanced T1-weighted images, and performs a brain tissue segmentation on the T2-weighted images and the contrast-enhanced T1-weighted images, so as to respectively yield a grey matter region, a white matter (WM) region, a cerebral spinal fluid (CSF) region, a bone region, and a soft tissue region.

In one embodiment of the present disclosure, calculating the ratio of the T2-weighted images to the contrast-enhanced T1-weighted images to generate contrast-enhanced images satisfies the following relationship: $SI(T2w/T1wC)=(SI(T2w)/WM\ mean\ SI(T2w))/(SI(T1wC)/WM\ mean\ SI(T1wC))$, where $SI(T2w/T1wC)$ is signal intensity of the contrast-enhanced images, $SI(T2w)$ is signal intensity of the T2-weighted image, WM mean $SI(T2w)$ is average signal intensity of the white matter region of the T2-weighted image, $SI(T1wC)$ is signal intensity of the contrast-enhanced T1-weighted images, WM mean $SI(T1wC)$ is average signal intensity of the white matter region of the contrast-enhanced T1-weighted images.

In one embodiment of the present disclosure, the unsupervised clustering eliminates extreme voxel signal intensity from the contrast-enhanced images through a median filter, and then divides the contrast-enhanced images into the cystic part and the non-cystic part through a fuzzy C-means clustering according to a difference in the signal intensity.

In one embodiment of the present disclosure, the result of the linear regression analysis indicates that in the feature parameters, a volume of the tumor, average signal intensity of the tumor in the contrast-enhanced images, average signal intensity of the cyst part in the contrast-enhanced images, average signal intensity of the non-cyst part in the contrast-enhanced images, an age, and a ratio of the cyst part to the tumor are respectively positively correlated with a volume reduction of the tumor after the radiosurgery.

Another embodiment of the present disclosure is related to an operation method of an automatic analysis system on MRI. The operation method includes steps of: receiving a plurality of images of a brain of a subjects brain from a MRI machine; obtaining contrast-enhanced T1-weighted images and T2-weighted images from the images, and performing a pre-processing on the images; calculating a ratio of the T2-weighted images to the contrast-enhanced T1-weighted images to generate contrast-enhanced images; performing an unsupervised clustering on a region of interest in the contrast-enhanced images to separate a cystic part and a non-cystic part so as to calculate feature parameters; analyzing a volume change of a tumor of the brain after radiosurgery is performed on the tumor corresponding to the region of interest; and performing a linear regression analysis of the feature parameters and the volume change of the tumor for prognostic evaluation.

In one embodiment of the present disclosure, the pre-processing performs a bias correction on the images, and then co-registers the T2-weighted images to the contrast-enhanced T1-weighted images, and performs a brain tissue segmentation on the T2-weighted images and the contrast-enhanced T1-weighted images, so as to respectively yield a grey matter region, a white matter (WM) region, a cerebral spinal fluid (CSF) region, a bone region, and a soft tissue region.

In one embodiment of the present disclosure, calculating the ratio of the T2-weighted images to the contrast-enhanced T1-weighted images to generate contrast-enhanced images satisfies the following relationship: $SI(T2w/T1wC)=(SI(T2w)/WM\ mean\ SI(T2w))/(SI(T1wC)/WM\ mean\ SI(T1wC))$, where $SI(T2w/T1wC)$ is signal intensity of the contrast-enhanced images, $SI(T2w)$ is signal intensity of the T2-weighted image, WM mean $SI(T2w)$ is average signal intensity of the white matter region of the T2-weighted image, $SI(T1wC)$ is signal intensity of the contrast-enhanced T1-weighted images, WM mean $SI(T1wC)$ is average signal intensity of the white matter region of the contrast-enhanced T1-weighted images.

In one embodiment of the present disclosure, the unsupervised clustering eliminates extreme voxel signal intensity from the contrast-enhanced images through a median filter, and then divides the contrast-enhanced images into the cystic part and the non-cystic part through a fuzzy C-means clustering according to a difference in the signal intensity.

In one embodiment of the present disclosure, the result of the linear regression analysis indicates that in the feature parameters, a volume of the tumor, average signal intensity of the tumor in the contrast-enhanced images, average signal intensity of the cyst part in the contrast-enhanced images, average signal intensity of the non-cyst part in the contrast-enhanced images, an age, and a ratio of the cyst part to the tumor are respectively positively correlated with a volume reduction of the tumor after the radiosurgery.

Technical advantages are generally achieved, by embodiments of the present disclosure. The technical solution of the present disclosure reliably establishes the regression model to evaluate the prognosis of tumor treatment.

Many of the attendant features will be more readily appreciated, as the same becomes better understood by reference to the following detailed description considered in connection with the accompanying drawings.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
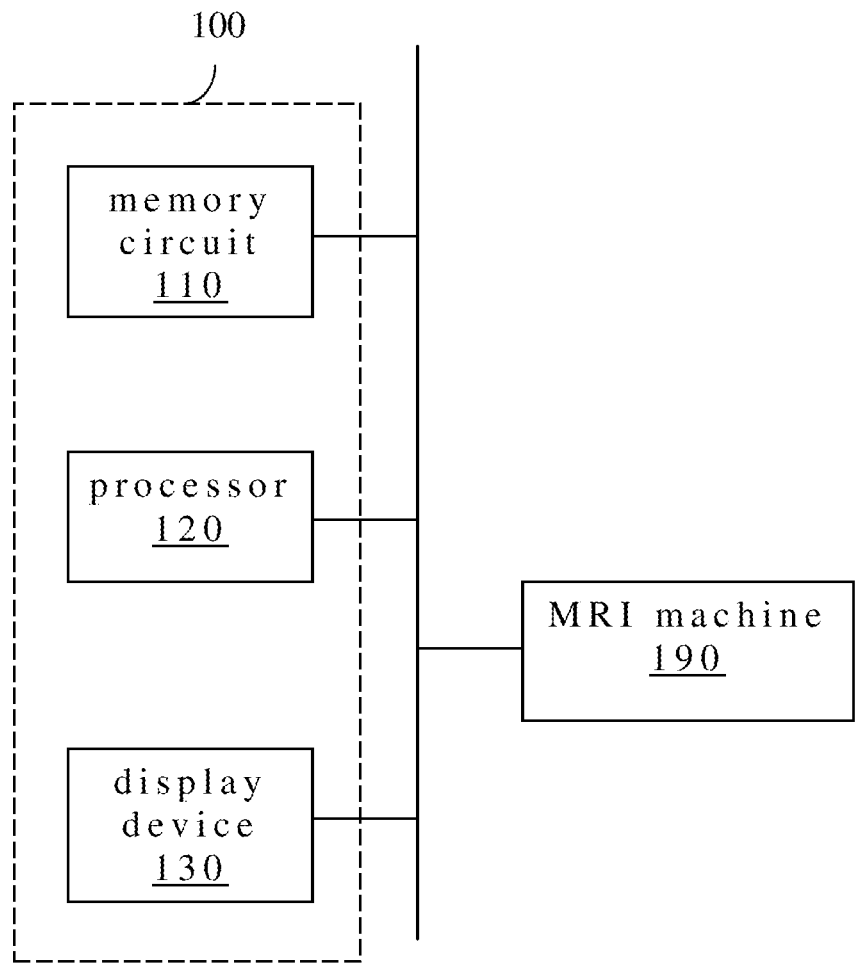
FIG. 1 is a block diagram of an automatic analysis system on MRI according to one embodiment of the present disclosure.

Reference will now be made in detail to the present embodiments of the invention, examples of which are illustrated in the accompanying drawings. Wherever possible, the same reference numbers are used in the drawings and the description to refer to the same or like parts.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a block diagram of an automatic analysis system 100 on MRI according to one embodiment of the present disclosure. As shown in FIG. 1, the automatic analysis system 100 includes a memory circuit 110, a processor 120 and a display device 130. For example, the memory circuit 110 can be a hard drive, a flash memory or another storage device, the processor 120 can be a central processing unit, and a display device 130 can be a built-in the display screen or an external screen.

In structure, the automatic analysis system 100 is coupled to a MRI machine 190, and the processor 120 is coupled to the memory circuit 110 and the display device 130.

In use, the memory circuit 110 store at least one instruction, the processor 120 is coupled to the memory circuit 110, and the processor 120 accesses and executes the at least one instruction for receiving a plurality of images of a brain of a subject's brain from a MRI machine; obtaining contrast-enhanced T1-weighted images and T2-weighted images from the images, and performing a pre-processing on the images; calculating a ratio of the T2-weighted images to the contrast-enhanced T1-weighted images to generate contrast-enhanced images; performing an unsupervised clustering on a region of interest in the contrast-enhanced images to separate a cystic part and a non-cystic part so as to calculate the feature parameters; analyzing a volume change of a tumor of the brain after radiosurgery is performed on the tumor corresponding to the region of interest; and performing a linear regression analysis of the feature parameters and the volume change of the tumor for prognostic evaluation.

In one embodiment of the present disclosure, the pre-processing performs a bias correction on the images, and then co-registers the T2-weighted images to the contrast-enhanced T1-weighted images, and performs a brain tissue segmentation on the T2-weighted images and the contrast-enhanced T1-weighted images, so as to respectively yield a grey matter region, a white matter (WM) region, a cerebral spinal fluid (CSF) region, a bone region, and a soft tissue region.

Cystic part of the tumor (e.g., vestibular schwannoma) usually shows low signal intensity (SI) on contrast-enhanced T1-weighted images and high SI on T2-weighted images, whereas non-cystic part usually shows high SI on contrast-enhanced T1-weighted images and low SI on T2-weighted images.

Thus, in order to enhance the contrast between the cystic part and the non-cystic part of the tumor and thereby improve the performance of fuzzy C-means clustering, in one embodiment of the present disclosure, the processor 120 accesses and executes the at least one instruction for calculating the ratio of the T2-weighted images to the contrast-enhanced T1-weighted images to generate contrast-enhanced images, which satisfies the following relationship: $SI(T2w/T1wC)=(SI(T2w)/WM\ mean\ SI(T2w))/(SI(T1wC)/WM\ mean\ SI(T1wC))$, where $SI(T2w/T1wC)$ is signal intensity of the contrast-enhanced images, $SI(T2w)$ is signal intensity of the T2-weighted image, WM mean SI(T2w) is average signal intensity of the white matter region of the T2-weighted image, SI(T1wC) is signal intensity of the contrast-enhanced T1-weighted images, WM mean SI (T1wC) is average signal intensity of the white matter region of the contrast-enhanced T1-weighted images.

Then, in one embodiment of the present disclosure, the unsupervised clustering eliminates extreme voxel signal intensity from the contrast-enhanced images through a median filter, and then divides the contrast-enhanced images into the cystic part and the non-cystic part through the fuzzy C-means clustering according to a difference in the signal intensity. Accordingly, the processor 120 accesses and executes the at least one instruction for calculating the feature parameters.

For example, the median filter can be implemented to remove the noises using Python. Fuzzy C-means clustering is an algorithm in which each data point (e.g., voxel) can belong to two clusters or more; according to the signal intensity difference, the voxels of the contrast-enhanced images are classified as the cystic part and the non-cystic part. In practice, the region of interest corresponding to the tumor can be manually set by the specialist or preset by the computer.

For example, the feature parameters includes radiological feature quantification, in which radiological features include average signal intensity of the tumor, average signal intensity of the cyst part, average signal intensity of the non-cyst part, a cystic part proportion, and cystic part shape features (e.g., spherecity, flatness, and elongation). In practice, the processor 120 accesses and executes the at least one instruction for averaging signal intensity of the region of interest in the contrast-enhanced images to calculate the average signal intensity of the tumor. The average signal intensity of the cyst part and the average signal intensity of the non-cyst part can be calculated by averaging the signal intensity of the cyst part and the non-cyst part respectively, segmented by fuzzy C-means clustering. The cystic part proportion is defined as the ratio of the volume of the cystic part to the volume of the tumor. The cystic part shape features, including spherecity, flatness and elongation, are obtained using the PyRadiomics package performed on the cystic part of the tumor.

After radiosurgery (e.g., Gamma Knife radiosurgery) is performed on the tumor (e.g., vestibular schwannoma) corresponding to the region of interest, MRI machine 190 can captures images after the radiosurgery and the processor 120 accesses and executes the at least one instruction for measuring the volume of the tumor based on the images after the radiosurgery, so as to analyze a volume change of the tumor at every follow-up neuroimaging. In practice, exponential fitting model was shown to be a fit for estimation of volumetric change of tumor after the radiosurgery; therefore, the tumor response to the radiosurgery is assessed by the specific growth rate (SGR), which was derived from the following formula: $SGR=\ln(Vt/Vo)/t$, where Vo is the volume of the tumor when the radiosurgery and Vt is the volume of the tumor at last follow-up, with t equaling the time period after the radiosurgery at last follow-up. In practice, the gender and age of the subject and the radiation dose of the radiosurgery can also be integrated into the above feature parameters.

As to the linear regression, in one embodiment of the present disclosure, the linear regression can be a univariate linear regression and/or a multivariate linear regression. The result of the linear regression analysis indicates that in the feature parameters, the volume of the tumor, the average signal intensity of the tumor in the contrast-enhanced images, the average signal intensity of the cyst part in the contrast-enhanced images, the average signal intensity of the non-cyst part in the contrast-enhanced images, the age, and the ratio of the cyst part to the tumor are respectively positively correlated with a volume reduction of the tumor after the radiosurgery. In other words, the volume of the tumor is larger, the average signal intensity of the tumor in the contrast-enhanced images is higher, the average signal intensity of the cyst part in the contrast-enhanced images is higher, the average signal intensity of the non-cyst part in the contrast-enhanced images is higher, the age is older, and/or the ratio of the cyst part to the tumor is higher; thus, the tumor after the radiosurgery is smaller. In this way, the display device 130 can show the result of the linear regression analysis for an effective basis of prognostic evaluation.

Figure 2:
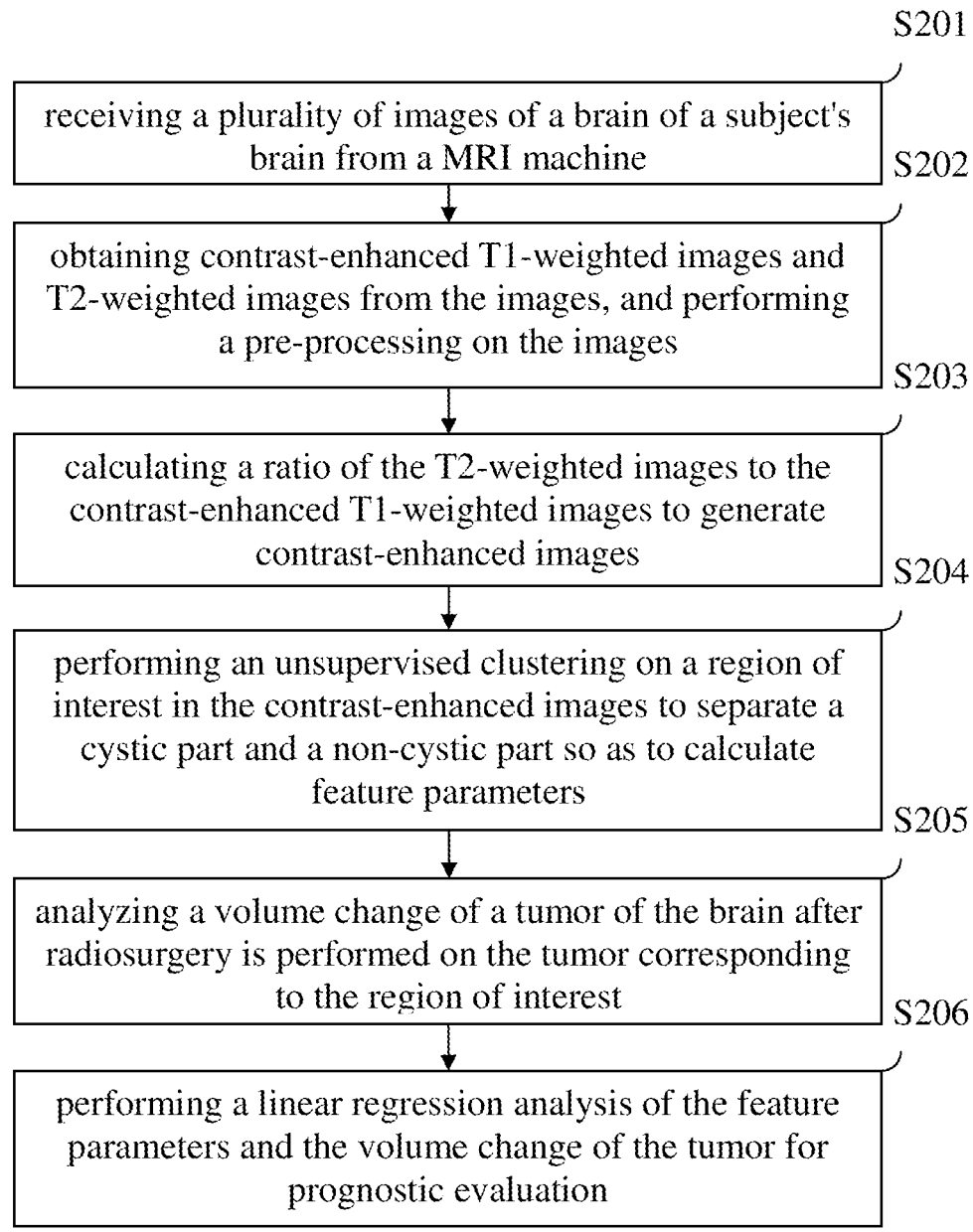
FIG. 2 is a flow chart of an operation method of the automatic analysis system according to one embodiment of the present disclosure.

For a more complete understanding of an operating method of the automatic analysis system 100 on MRI, referring FIGS. 1-2, FIG. 2 is a flow chart of the operation method 200 of the automatic analysis system 100 according to one embodiment of the present disclosure. As shown in FIG. 2, the operation method 200 includes operations S201-S206. However, as could be appreciated by persons having ordinary skill in the art, for the steps described in the present embodiment, the sequence in which these steps is performed, unless explicitly stated otherwise, can be altered depending on actual needs; in certain cases, all or some of these steps can be performed concurrently.

In operation S201, Images are received from of the subject's brain from the MRI machine. In operation S202, contrast-enhanced T1-weighted images and T2-weighted images are obtained from the images, and the pre-processing is performed on the images. In operation S203, the ratio of T2-weighted images to contrast-enhanced T1-weighted images is calculated to generate contrast-enhanced images. In operation S204, the unsupervised clustering is performed on the region of interest in the contrast-enhanced image to separate a cystic part and a non-cystic part so as to calculate the feature parameters. In operation S205, after radiosurgery is performed on the brain tumor corresponding to the region of interest, the volume change of the tumor is analyzed. In operation S206, the linear regression analysis of the feature parameters and the volume change of the tumor is performed for prognostic evaluation.

In one embodiment of the present disclosure, in operation S202, the pre-processing performs a bias correction on the images, and then co-registers the T2-weighted images to the contrast-enhanced T1-weighted images, and performs a brain tissue segmentation on the T2-weighted images and the contrast-enhanced T1-weighted images, so as to respectively yield a grey matter region, a white matter (WM) region, a cerebral spinal fluid (CSF) region, a bone region, and a soft tissue region.

In one embodiment of the present disclosure, in operation S203, calculating the ratio of the T2-weighted images to the contrast-enhanced T1-weighted images to generate contrast-enhanced images satisfies the following relationship: SI(T2w/T1wC)=(SI(T2w)/WM mean SI(T2w))/(SI(T1wC)/ WM mean SI(T1wC)), where SI(T2w/T1wC) is signal intensity of the contrast-enhanced images, SI(T2w) is signal intensity of the T2-weighted image, WM mean SI(T2w) is average signal intensity of the white matter region of the T2-weighted image, SI(T1wC) is signal intensity of the contrast-enhanced T1-weighted images, WM mean SI (T1wC) is average signal intensity of the white matter region of the contrast-enhanced T1-weighted images.

In one embodiment of the present disclosure, in operation S204, the unsupervised clustering eliminates extreme voxel signal intensity from the contrast-enhanced images through a median filter, and then divides the contrast-enhanced images into the cystic part and the non-cystic part through a fuzzy C-means clustering according to a difference in the signal intensity.

In one embodiment of the present disclosure, in operation S206, the result of the linear regression analysis indicates that in the feature parameters, a volume of the tumor, average signal intensity of the tumor in the contrast-enhanced images, average signal intensity of the cyst part in the contrast-enhanced images, average signal intensity of the non-cyst part in the contrast-enhanced images, an age, and a ratio of the cyst part to the tumor are respectively positively correlated with a volume reduction of the tumor after the radiosurgery.

In view of above, technical advantages are generally achieved, by embodiments of the present disclosure. The technical solution of the present disclosure reliably establishes the regression model to evaluate the prognosis of tumor treatment.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An automatic analysis system on magnetic resonance imaging (MRI), comprising:
   a memory circuit configured to store at least one instruction; and
   a processor coupled to the memory circuit, and the processor configured to access and execute the at least one instruction for:
      receiving a plurality of images of a brain of a subject's brain from a MRI machine;
      obtaining contrast-enhanced T1-weighted images and T2-weighted images from the images, and performing a pre-processing on the images;
      calculating a ratio of the T2-weighted images to the contrast-enhanced T1-weighted images to generate contrast-enhanced images;
      performing an unsupervised clustering on a region of interest in the contrast-enhanced images to separate a cystic part and a non-cystic part so as to calculate feature parameters;
      analyzing a volume change of a tumor of the brain after radiosurgery is performed on the tumor corresponding to the region of interest; and
      performing a linear regression analysis of the feature parameters and the volume change of the tumor for prognostic evaluation.

2. The automatic analysis system on MRI of claim 1, wherein the pre-processing performs a bias correction on the images, and then co-registers the T2-weighted images to the contrast-enhanced T1-weighted images, and performs a brain tissue segmentation on the T2-weighted images and the contrast-enhanced T1-weighted images, so as to respectively yield a grey matter region, a white matter (WM) region, a cerebral spinal fluid (CSF) region, a bone region, and a soft tissue region.

3. The automatic analysis system on MRI of claim 2, wherein calculating the ratio of the T2-weighted images to the contrast-enhanced T1-weighted images to generate contrast-enhanced images satisfies the following relationship:
$SI(T2w/T1wC)=(SI(T2w)/WM \text{ mean } SI(T2w))/(SI(T1wC)/WM \text{ mean } SI(T1wC))$, where $SI(T2w/T1wC)$ is signal intensity of the contrast-enhanced images, $SI(T2w)$ is signal intensity of the T2-weighted image, WM mean $SI(T2w)$ is average signal intensity of the white matter region of the T2-weighted image, $SI(T1wC)$ is signal intensity of the contrast-enhanced T1-weighted images, WM mean SI $(T1wC)$ is average signal intensity of the white matter region of the contrast-enhanced T1-weighted images.

4. The automatic analysis system on MRI of claim 3, wherein the unsupervised clustering eliminates extreme voxel signal intensity from the contrast-enhanced images through a median filter, and then divides the contrast-enhanced images into the cystic part and the non-cystic part through a fuzzy C-means clustering according to a difference in the signal intensity.

5. The automatic analysis system on MRI of claim 4, wherein the result of the linear regression analysis indicates that in the feature parameters, a volume of the tumor, average signal intensity of the tumor in the contrast-enhanced images, average signal intensity of the cyst part in the contrast-enhanced images, average signal intensity of the non-cyst part in the contrast-enhanced images, an age, and a ratio of the cyst part to the tumor are respectively positively correlated with a volume reduction of the tumor after the radiosurgery.

6. An operating method of an automatic analysis system on MRI, and the operating method comprising:
   receiving a plurality of images of a brain of a subject's brain from a MRI machine;
   obtaining contrast-enhanced T1-weighted images and T2-weighted images from the images, and performing a pre-processing on the images;
   calculating a ratio of the T2-weighted images to the contrast-enhanced T1-weighted images to generate contrast-enhanced images;
   performing an unsupervised clustering on a region of interest in the contrast-enhanced images to separate a cystic part and a non-cystic part so as to calculate feature parameters;
   analyzing a volume change of a tumor of the brain after radiosurgery is performed on the tumor corresponding to the region of interest; and
   performing a linear regression analysis of the feature parameters and the volume change of the tumor for prognostic evaluation.

7. The operating method of claim 6, wherein the pre-processing performs a bias correction on the images, and then co-registers the T2-weighted images to the contrast-enhanced T1-weighted images, and performs a brain tissue segmentation on the T2-weighted images and the contrast-enhanced T1-weighted images, so as to respectively yield a grey matter region, a white matter (WM) region, a cerebral spinal fluid (CSF) region, a bone region, and a soft tissue region.

8. The operating method of claim 7, wherein calculating the ratio of the T2-weighted images to the contrast-enhanced T1-weighted images to generate contrast-enhanced images satisfies the following relationship:
$SI(T2w/T1wC)=(SI(T2w)/WM \text{ mean } SI(T2w))/(SI(T1wC)/WM \text{ mean } SI(T1wC))$, where $SI(T2w/T1wC)$ is signal intensity of the contrast-enhanced images, $SI(T2w)$ is signal intensity of the T2-weighted image, WM mean $SI(T2w)$ is an average signal intensity of the white matter region of the T2-weighted image, SI(T1wC) is signal intensity of the contrast-enhanced T1-weighted images, WM mean SI (T1wC) is average signal intensity of the white matter region of the contrast-enhanced T1-weighted images.

9. The operating method of claim 8, wherein the unsupervised clustering eliminates extreme voxel signal intensity from the contrast-enhanced images through a median filter, and then divides the contrast-enhanced images into the cystic part and the non-cystic part through a fuzzy C-means clustering according to a difference in the signal intensity.

10. The operating method of claim 9, wherein the result of the linear regression analysis indicates that in the feature parameters, a volume of the tumor, average signal intensity of the tumor in the contrast-enhanced images, average signal intensity of the cyst part in the contrast-enhanced images, average signal intensity of the non-cyst part in the contrast-enhanced images, an age, and a ratio of the cyst part to the tumor are respectively positively correlated with a volume reduction of the tumor after the radiosurgery.

* * * * *